(12) United States Patent
Liao et al.

(10) Patent No.: US 8,852,423 B2
(45) Date of Patent: Oct. 7, 2014

(54) ELECTROCHEMICAL TEST STRIP AND METHOD FOR TESTING A SAMPLE USING THE SAME

(71) Applicant: DELBio, Inc, Taoyuan Hsien (TW)

(72) Inventors: Hung-Yun Liao, Taoyuan Hsien (TW); Chi-Yan Chen, Taoyuan Hsien (TW); Cheng-Chuan Chen, Taoyuan Hsien (TW)

(73) Assignee: DELBio, Inc., Taoyuan Hsien (TW)

( * ) Notice: Subject to any disclaimer, the term of this patent is extended or adjusted under 35 U.S.C. 154(b) by 0 days.

(21) Appl. No.: 13/739,801

(22) Filed: Jan. 11, 2013

(65) Prior Publication Data

US 2013/0180869 A1 Jul. 18, 2013

Related U.S. Application Data (60) Provisional application No. 61/586,907, filed on Jan. 16, 2012.

(51) Int. Cl.
*G01N 27/26* (2006.01)
*G01N 27/327* (2006.01)

(52) U.S. Cl.
CPC ........ *G01N 27/3275* (2013.01); *G01N 27/3274* (2013.01)
USPC ....................................... 205/792; 205/777.5

(58) Field of Classification Search
USPC ............. 204/403.01–403.15; 205/777.5, 778, 205/792
See application file for complete search history.

(56) References Cited

U.S. PATENT DOCUMENTS

| | | | | |
|---|---|---|---|---|
| 5,650,062 A | * | 7/1997 | Ikeda et al. | 205/778 |
| 7,138,041 B2 | * | 11/2006 | Su et al. | 204/403.04 |
| 7,288,174 B2 | | 10/2007 | Cui et al. | |
| 7,655,128 B2 | * | 2/2010 | Hsu et al. | 205/775 |
| 7,695,600 B2 | | 4/2010 | Ho et al. | |
| 8,354,012 B2 | * | 1/2013 | Reid et al. | 204/403.04 |
| 2009/0000959 A1 | * | 1/2009 | Feldman et al. | 205/777.5 |

FOREIGN PATENT DOCUMENTS

| | | |
|---|---|---|
| TW | M287818 | 2/2006 |
| TW | 201102647 | 7/2009 |
| TW | 201120444 | 6/2011 |
| TW | 201129800 | 9/2011 |
| TW | 201142285 | 12/2011 |

* cited by examiner

*Primary Examiner* — Alex Noguerola
(74) *Attorney, Agent, or Firm* — Muncy, Geissler, Olds & Lowe, P.C.

(57) ABSTRACT

An electrochemical test strip is provided, including a substrate, an electrode structure and an insulative film. The electrode structure is formed on the substrate, including a first electrode and a second electrode. The second electrode includes a first end, a second end, an extension portion, and a bent portion. The extension portion connects the first end with the bent portion, and the bent portion is connected to the second end. The extension portion and the first electrode define a space therebetween for receiving the bent portion. The insulative film covers at least a part of the electrode structure and forms an opening. A sample fluid enters the electrochemical test strip through the opening, and the sample fluid sequentially contacts the first electrode and the second electrode.

12 Claims, 13 Drawing Sheets

ELECTROCHEMICAL TEST STRIP AND METHOD FOR TESTING A SAMPLE USING THE SAME

CROSS REFERENCE TO RELATED APPLICATIONS

This application claims the benefit of U.S. Provisional Application No. 61/586,907, filed on Jan. 16, 2012, the entirety of which is incorporated by reference.

BACKGROUND OF THE INVENTION

1. Field of the Invention

The present invention relates to an electrochemical test strip, and in particular relates to an electrochemical test strip with an underfill detection function.

2. Description of the Related Art

Figure 1:
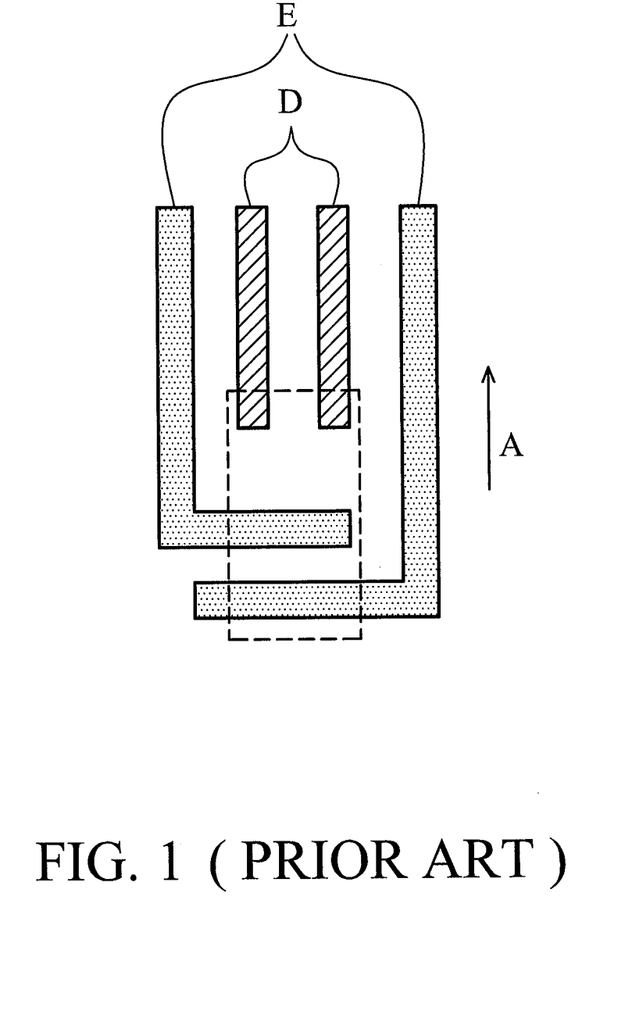
FIG. 1 is a schematic view of identifying electrodes and reaction electrodes of a conventional electrochemical test strip.

Referring to FIG. 1, a conventional electrochemical test strip comprises a set of identifying electrodes D, insulated from each other. When a sample is injected into the strip and through a set of reaction electrodes E to the set of identifying electrodes D along a direction A, the set of identifying electrodes D are electrically conducted through the sample to form a circuit. The circuit can be electrically connected to an instrument for determining fill or under fill of the sample.

However, the conventional electrochemical test strip requires at least two pins for the additional set of identifying electrodes, thus reducing the number of available pins and obstructing the expansion for other functions.

Further more, a conventional electrode structure comprises a reaction area between an upper electrode and a lower electrode (face to face structure) for determining the hematocrit ratio by flowing speed. When the sample contacts the reagent in the reaction area, the electronic signal between the upper and lower electroedes starts to highly increase by the chemical reaction between the sample and the reagent, when the sample contacts electrode without reagent, the electronic signal starts to highly decrease, and the time interval between the highly increasing and decreasing times of the electronic signal can be used to calculate flowing speed and the hematocrit ratio of the sample. However, the electrodes of the face to face structure could be conducted to each other by compressing the strip, and the flowing speed could be affected by the coating of the reagent on the reaction area.

BRIEF SUMMARY OF THE INVENTION

The present invention provides an electrochemical test strip, comprising a substrate, an electrode structure, and an insulative layer. The substrate comprises a test end. The electrode structure is formed on the substrate, comprising: a first electrode and a second electrode. The second electrode comprises a first end, a second end, an extension portion and a bent portion, wherein the extension portion is connected between the first end and the bent portion, the bent portion is connected to the second end, and the extension portion and the first electrode define a space therebetween for receiving the bent portion. The insulative layer covers at least a part of the electrode structure and forms an opening, wherein a sample is injected through the opening into the electrochemical test strip and sequentially contacts the first electrode and the second electrode.

BRIEF DESCRIPTION OF THE DRAWINGS

The present invention can be more fully understood by reading the subsequent detailed description and examples with references made to the accompanying drawings, wherein.

DETAILED DESCRIPTION OF THE INVENTION

Figure 2:
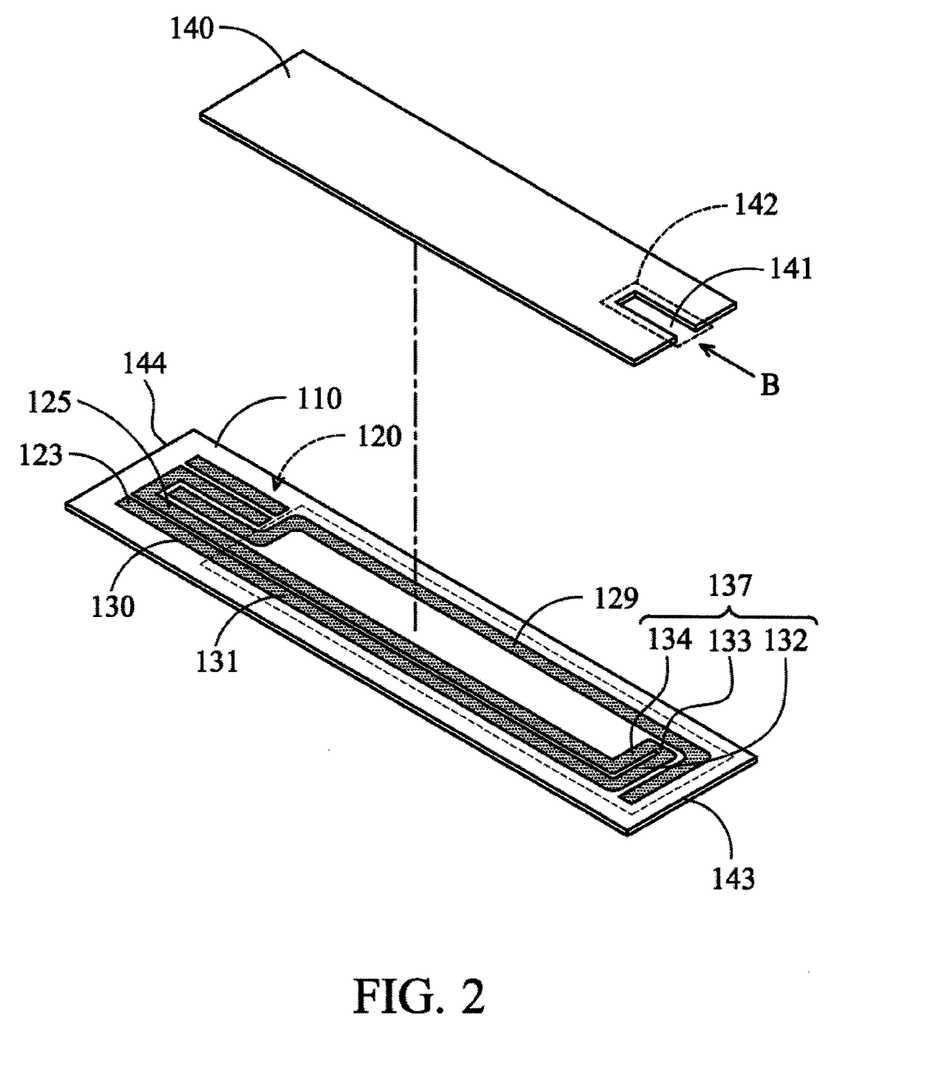
FIG. 2 is an exploded diagram of an electrochemical test strip according to an embodiment of the invention.

Referring to FIG. 2, an embodiment of an electrochemical test strip comprises a substrate 110, an electrode structure 120 and an insulative layer 140. The electrode structure 120 is formed on the substrate 110 which comprises a test end 143 and a connection end 144. The insulative layer 140 covers at least a part of the electrode structure 120 and an opening 141 is formed in the insulative layer 140 corresponding to the test end 143. An uncovered area of the insulative layer 140 relative to the electrode structure 120 is as a reaction area 142. Specifically, the electrode structure 120 may comprise non-metal material such as carbon. In some embodiments, the electrode structure 120 may comprise non-metal and metal materials, wherein the metal material may be gold, silver, palladium, platinum, nickel, copper, molybdenum, cobalt, chromium, zinc, tin, plumbum, or titanium. However the electrode structure 120 may only comprise metal material.

Referring to FIG. 2 and FIG. 3, the electrode structure 120 comprises a working electrode 129 and an auxiliary electrode 130. The auxiliary electrode 130 comprises an extension portion 131, a bent portion 137, a first end 123, and a second end 125. The extension portion 130 is connected between the first end 123 and the bent portion 137, and the bent portion 137 is connected to the second end 125. The first end 123 and second 125 are disposed at the connection end 144 of the substrate 110, and a detection signal can be sent out through the first end 123 and the second end 125. As shown in FIG. 3a, the working electrode 129 is extended and forms a bent structure (the lower section of FIG. 3a), wherein the extension portion 131 and the working electrode 129 form a space 136 with the bent portion 137 disposed therein.

Figure 3A:
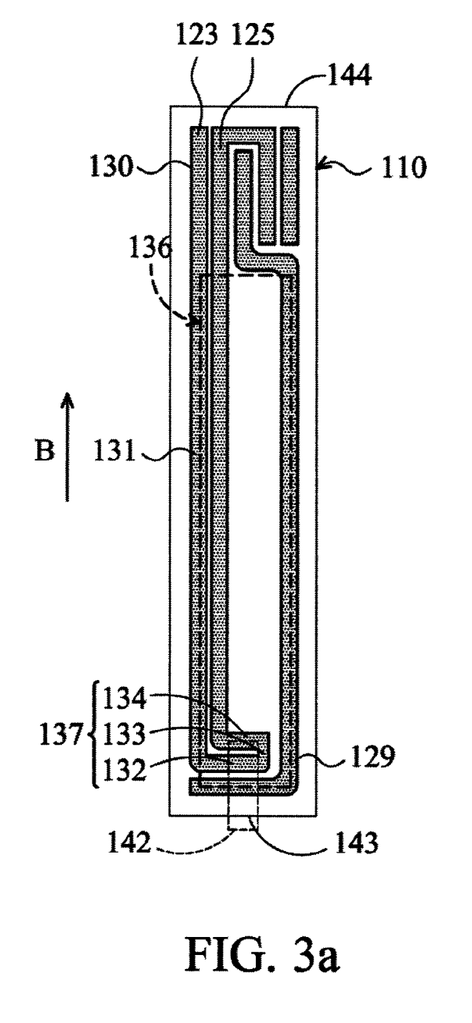
FIG. 3a is a schematic view showing a substrate and an electrode structure of an electrochemical test strip according to another embodiment of the invention.

The bent portion 137 in FIG. 3a comprises a first section 132, a connecting section 133, and a second section 134, wherein the first section 132 is connected between the extension portion 131 and the connecting section 133, and the second section 134 is connected between the second end 125 and the connecting section 133. The first section 132, the second section 134, and the connecting section 133 form a U-shaped structure, having an opening toward the extension portion 131. Specifically, the opening of the U-shaped structure may also face toward the test end 143 depending on design requirements.

Figure 6:
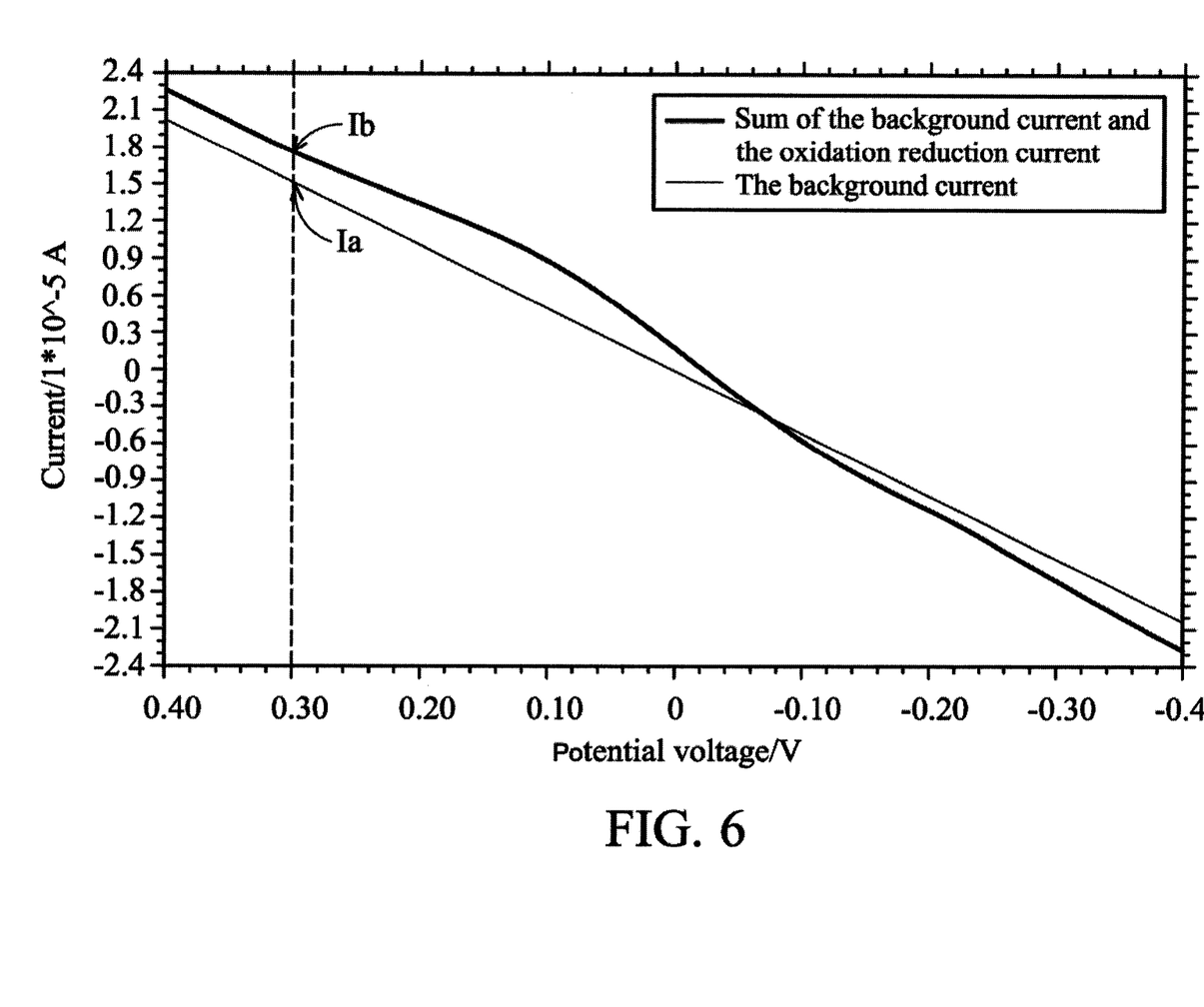
FIG. 6 is a schematic view showing variation of an electrical current when detecting underfill of a sample in an electrochemical test strip according to an embodiment of the invention.

The detection process will be described below. First, the first end 123 and the second end 125 are provided with a small voltage. A sample (such as blood) can be injected through the opening 141 into the reaction area 142 and sequentially move through the working electrode 129, the first section 132, and the second section 134 along an injection direction B. FIG. 6 illustrates a result of the cyclic voltammetry between the first end 123 and the second end 125. Before the sample flows into the reaction area 142, only a background current Ia can be measured. When the sample is underfilled, the working electrode 129 and the first section 132 are covered by the sample, and only the background current Ia is measured. When the sample covers the second section 134, the first and the second sections 132 and 134 are electrically conducted by the sample, and the sample undergoes an electrochemical reaction. With the cyclic voltammetry applied to the electrochemical test strip, an oxidation-reduction current can be produced, such that, a total current Ib of the background current and the oxidation reduction can be measured. As fill or underfill of the sample in the reaction area 142 can be determined by measuring the electrical current, a more precise result of measurement can be achieved.

Figure 7A:
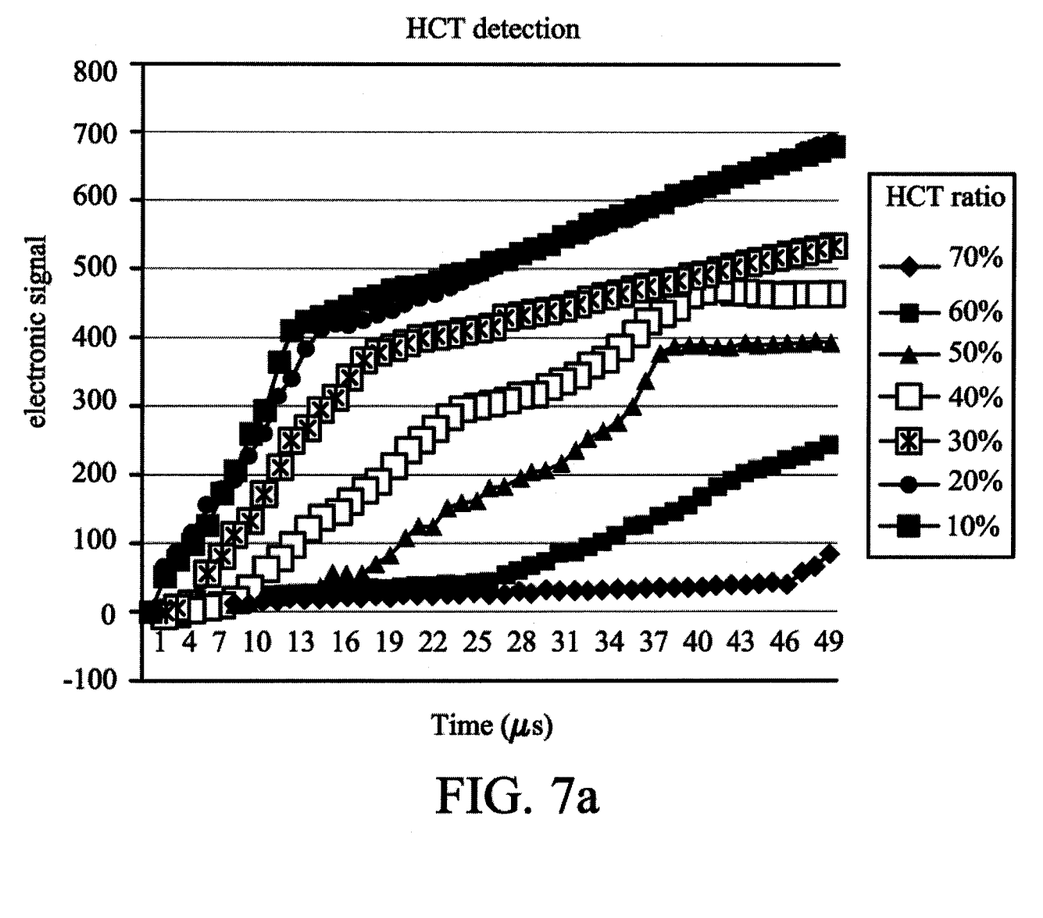
FIG. 7a is a schematic view showing variation of electronic signals with different hematocrit (HCT) ratios of samples.
Figure 7B:
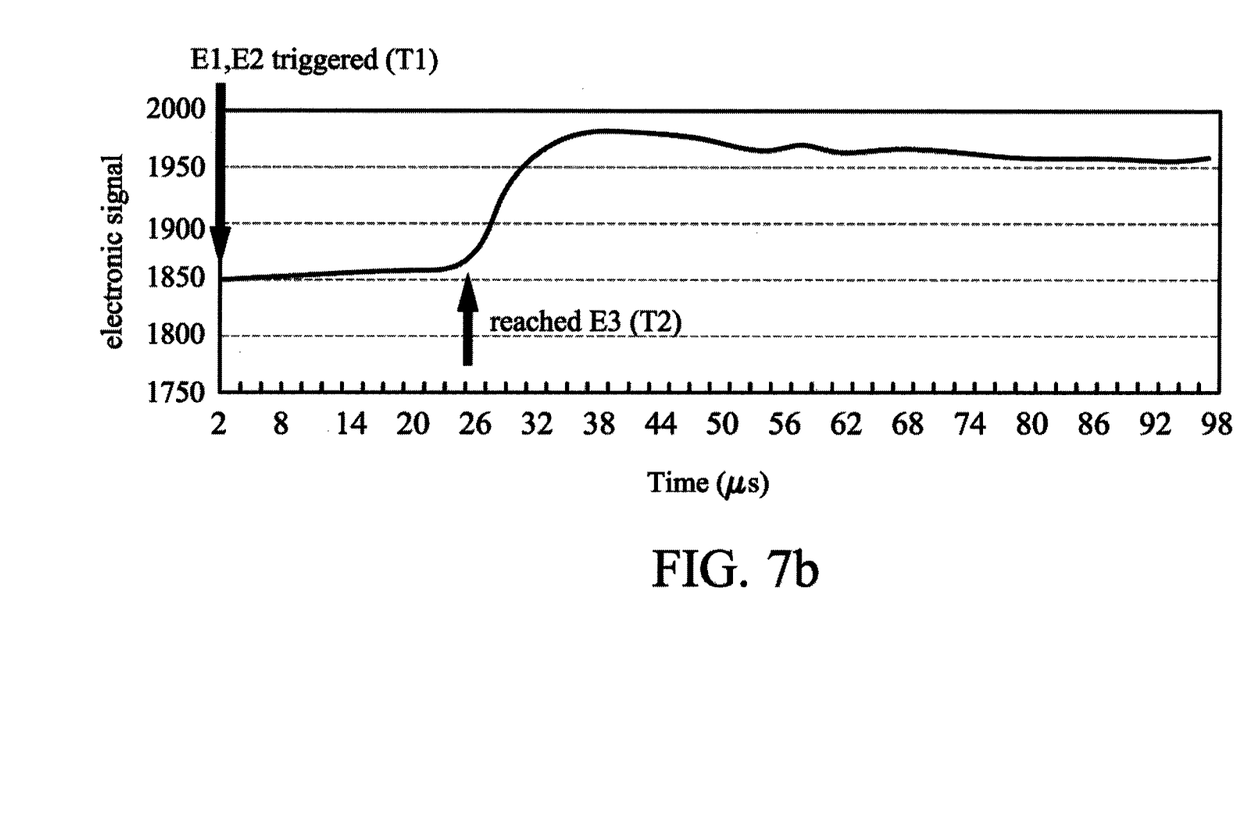
FIG. 7b is a schematic view showing variation of an electronic signal between second and third electrodes according to a testing voltage.
Figure 8A:
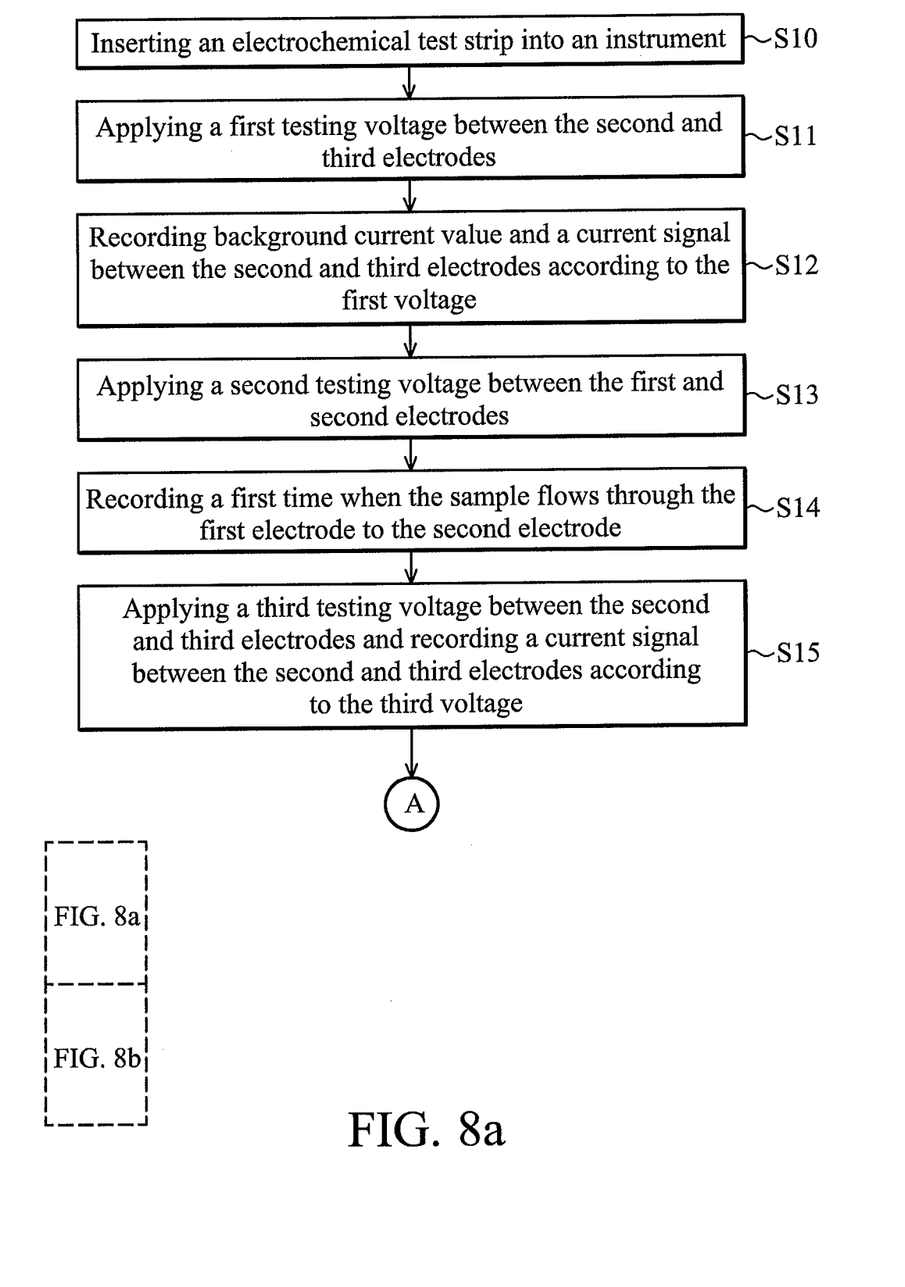
FIGS. 8a and 8b are flowcharts of an embodiment of the method for testing a sample by an electrochemical test strip.
Figure 8B:
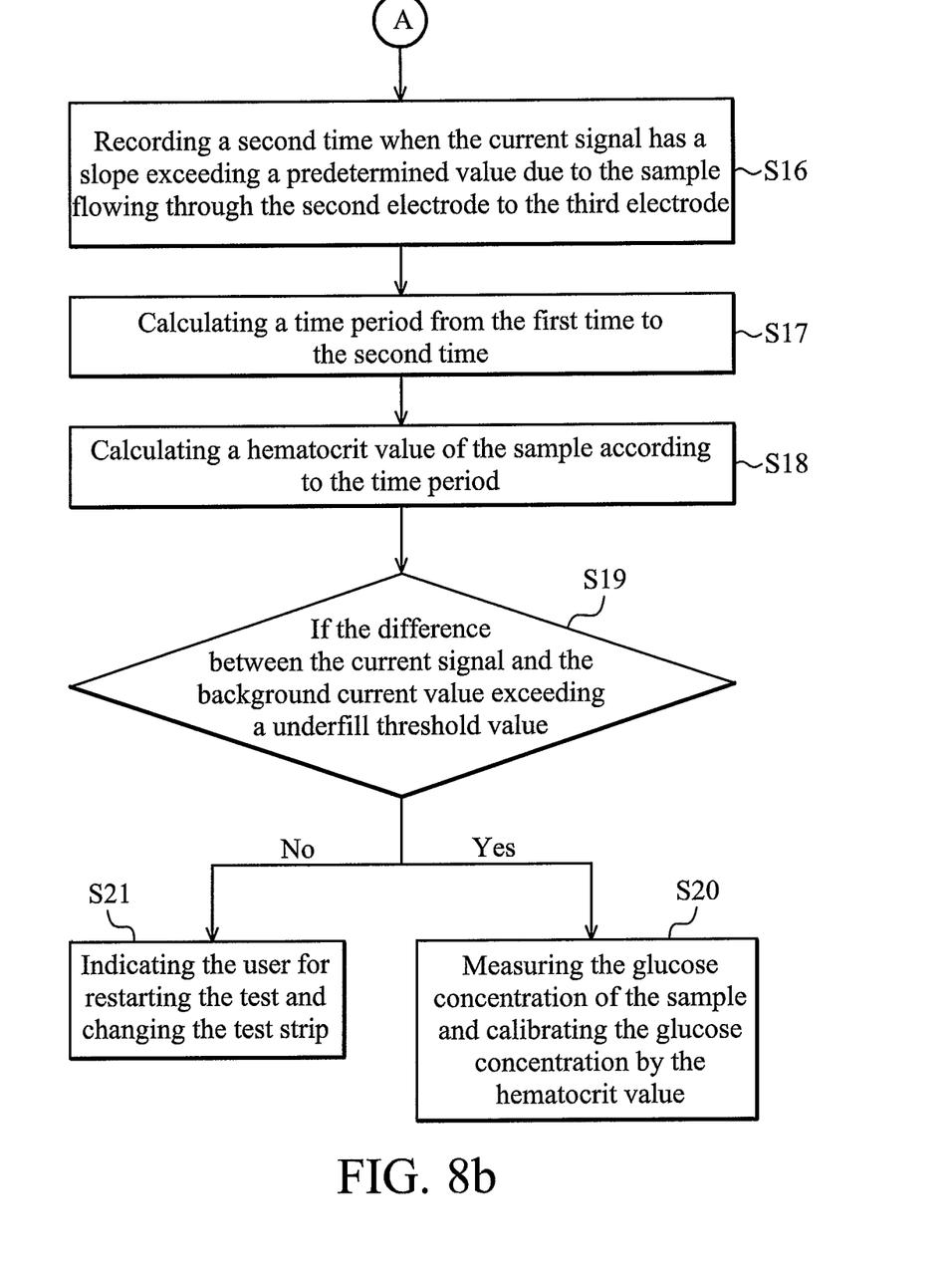

In some embodiments, the electrochemical test strip can be used for determining the hematocrit ratio of a sample. As shown in FIG. 7a, the electronic signal curves show different pattern correspond to several samples having different hematocrit ratios. The sample has higher flowing speed with lower hematocrit ratio. Thus, the hematocrit ratio of the sample can be determined by measuring a time interval during the sample flowing from an electrode (first time T1) to another electrode (second time T2), wherein the second time T2 is recoded when the slope of the electronic signal exceeds to a predetermined value (as shown in FIG. 7b). FIGS. 8a and 8b shows a method for testing a sample by an electrochemical test strip as shown in FIGS. 9a and 9b, wherein the electrochemical test strip includes a first electrode 210, a second electrode 220 insulated from the first electrode 210, and a third electrode 230 connected to the second electrode 220.

Figure 9A:
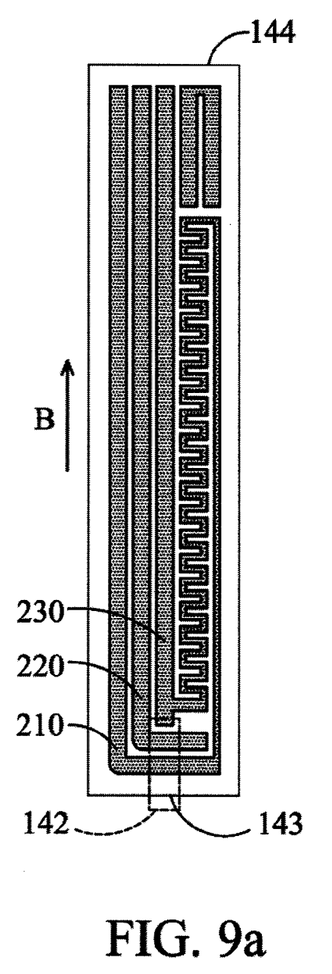
FIGS. 9a and 9b are sectional schematic views showing an electrode structure of an electrochemical test strip for testing a sample.
Figure 9B:
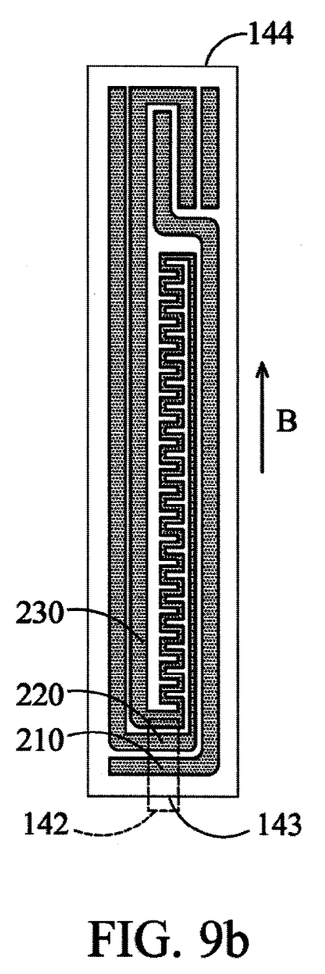

As shown in FIGS. 8a and 8b, first, an electrochemical test strip of FIG. 9a or 9b is inserted into an instrument (step S10). A first testing voltage is then applied between the second electrode 220 and the third electrode 230 for recording a background current value therebetween (steps S11~S12). Before the sample be injected into the strip, the instrument applies a second testing voltage between the first electrode 210 and the second electrode 220, and the instrument records a first time T1 when the sample flows through the first electrode 210 to the second electrode 220 (steps S13~S14). After recording the first time T1, the instrument applies a third testing voltage between the second electrode 220 and the third electrode 230 for recording a current signal between the second electrode 220 and the third electrode 230 (step S15). In an embodiment of the invention, the third testing voltage may be just as same volume as what the first testing voltage is, however, the third testing voltage can also be different volume with what the first testing voltage is.

Specifically, when the current signal has a slope exceeding a predetermined value due to the sample flowing through the second electrode 220 to the third electrode 230, a second time T2 is recorded (step S16). The hematocrit value of the sample can be calculated according to the time period T from the first time T1 to the second time T2, wherein T=T2−T1 (steps S17~S18).

Fill or underfill of the sample in the reaction area 142 may be also determined according to the difference between the current signal and the background current value (step 19). If the difference between the current signal and the background current value exceeds a threshold value, the instrument may change to apply a third testing voltage between the first electrode 210 and the second electrode 220 for measuring the glucose concentration of the sample, and the glucose concentration can also be calibrated by the hematocrit value (step 20). Otherwise, the instrument may further prompt the user to change the electrochemical test strip if the difference between the background current value and the current signal is less than a threshold value (step 21).

Figure 3B:
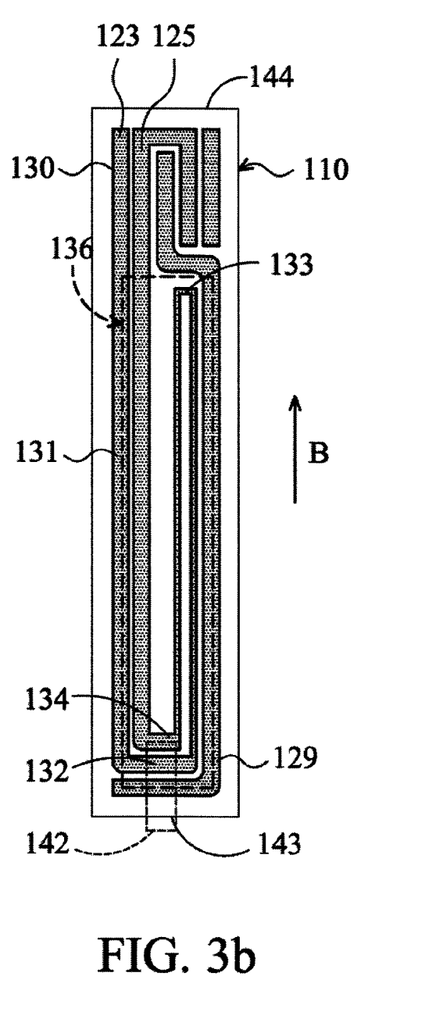
FIG. 3b is a schematic view showing a substrate and an electrode structure of an electrochemical test strip according to another embodiment of the invention.

Referring to FIGS. 3b to 3e, several different bent portions 137 are provided for increasing the impedance and the potential difference between the first section 132 and the second section 134. Namely, the chemical driving force between the first section 132 and the second section 134 can be strengthened, and the oxidation reduction current can be increased, thus enhancing the sensitivity of underfill detection. FIG. 3b is another embodiment of the bent portion 137, wherein the shape of the connecting section 133 of the bent portion 137 is changed to increase the resistance thereof. As shown in FIG. 3b, the connecting section 133 is connected between the first section 132 and the second section 134 and forms a U-shaped structure, wherein the U-shaped structure has an opening toward the test end 143. Specifically, the opening of the U-shaped structure may also face toward the extension portion 131.

Figure 3C:
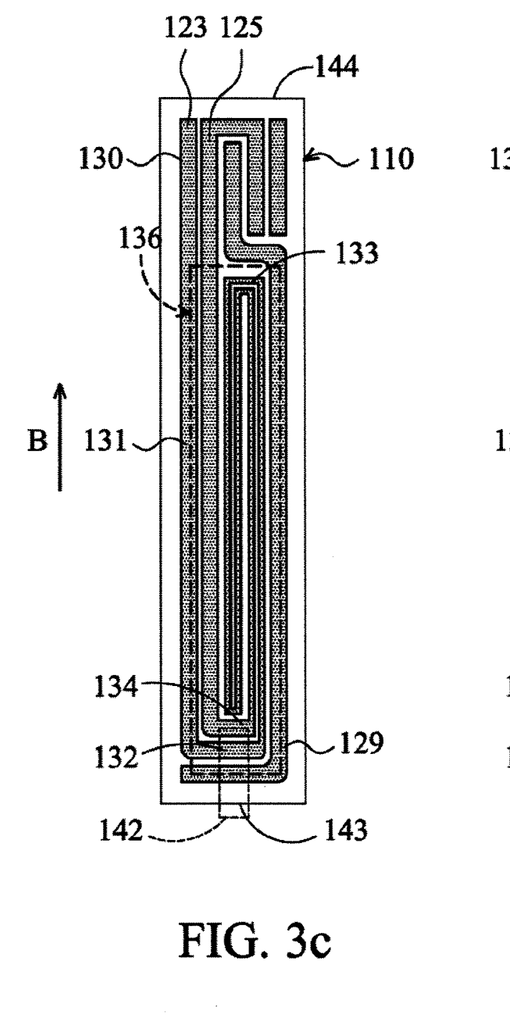
FIG. 3c is a schematic view showing a substrate and an electrode structure of an electrochemical test strip according to another embodiment of the invention.

Referring to FIG. 3c, another embodiment of a connecting section 133 is connected between the first section 132 and the second section 134, and forms a hollow U-shaped structure, wherein the hollow U-shaped structure has an opening toward the test end 143. However, the opening of the hollow U-shaped structure may also face toward the extension portion 133.

Figure 3D:
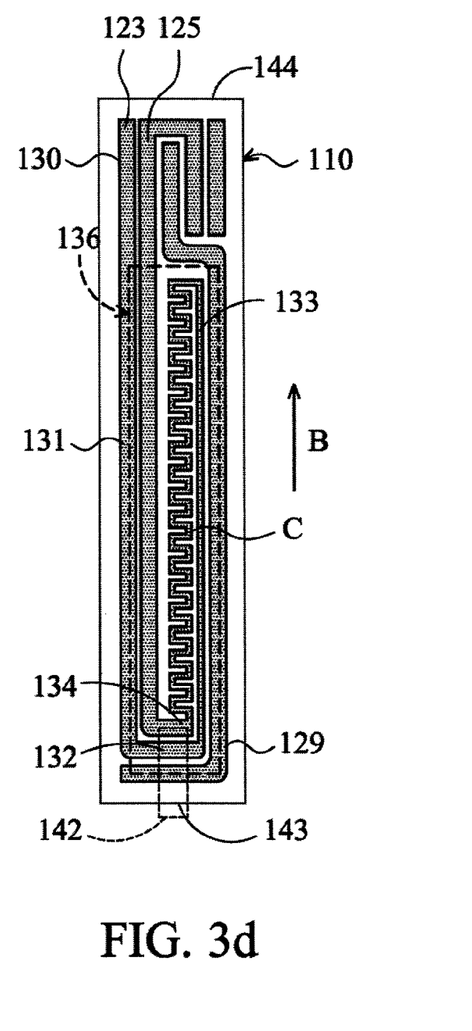
FIG. 3d is a schematic view showing a substrate and an electrode structure of an electrochemical test strip according to another embodiment of the invention.

Referring to FIG. 3d, another embodiment of the connecting section 133 is connected between the first section 132 and the second section 134 and forms a comb-shaped structure C, wherein the comb-shaped structure C has an opening toward the extension portion 133. However, the opening of the comb-shaped structure C may also face toward the test end 143.

In this embodiment, the comb-shaped structure C has right angled teeth. In some embodiments, the comb-shaped structure C may have rounded or acute angled teeth. The traces of the comb-shaped structure C may have a width, ranging from 0.1 to 1 mm. However, the traces may also respectively have different widths, to provide different densities thereof. Furthermore, the comb-shaped structure C may also have a spacing width between the traces, ranging from 0.1 to 1 mm.

However, the comb-shaped structure C may respectively have different spacing widths between the traces, to provide different densities thereof. In some embodiments, the comb-shaped structure C can be produced by various kinds of processes, such as screen printing, laser ablation, sputtering, or electroless plating processes, but is not limited thereto.

Figure 3E:
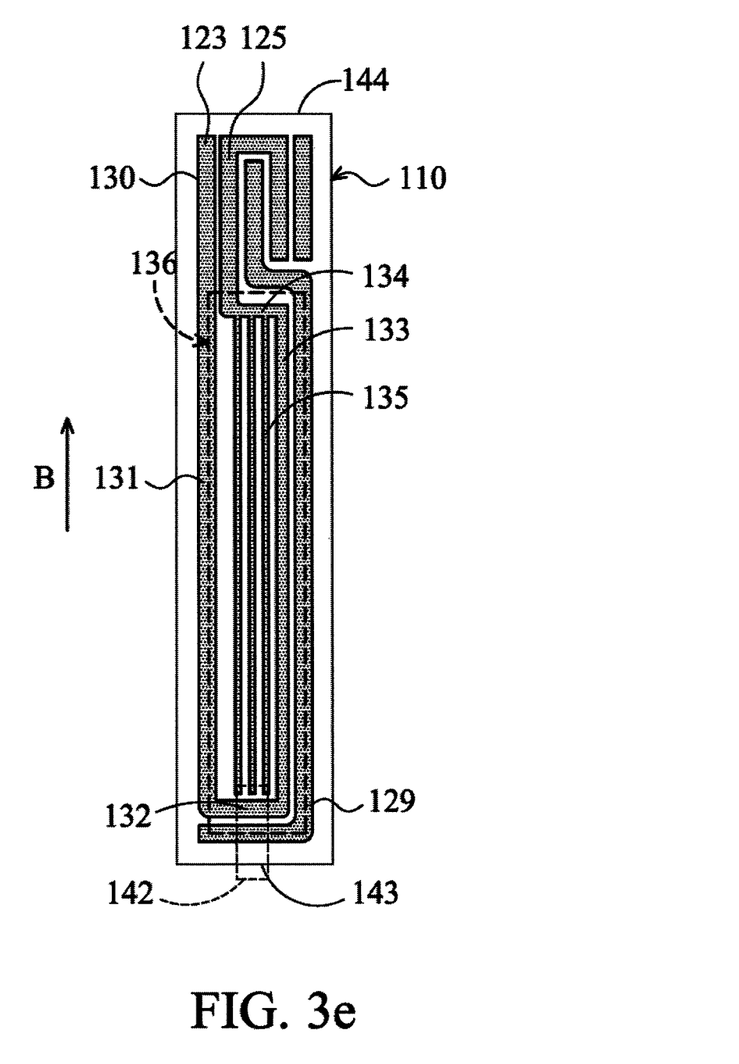
FIG. 3e is a schematic view showing a substrate and an electrode structure of an electrochemical test strip according to another embodiment of the invention.

The underfill of the sample may also be detected by using different protruding sections, thus preventing erroneous detections. Referring to FIG. 3e, another embodiment of the connecting section 133 is connected between the first section 132 and the second section 134, wherein the first section 132, the second section 134, and the connecting section 133 form a U-shaped structure. The bent portion 137 further comprises at least one protruding section 135, connected to the second section 134 and extended toward the test end 143.

Figure 4:
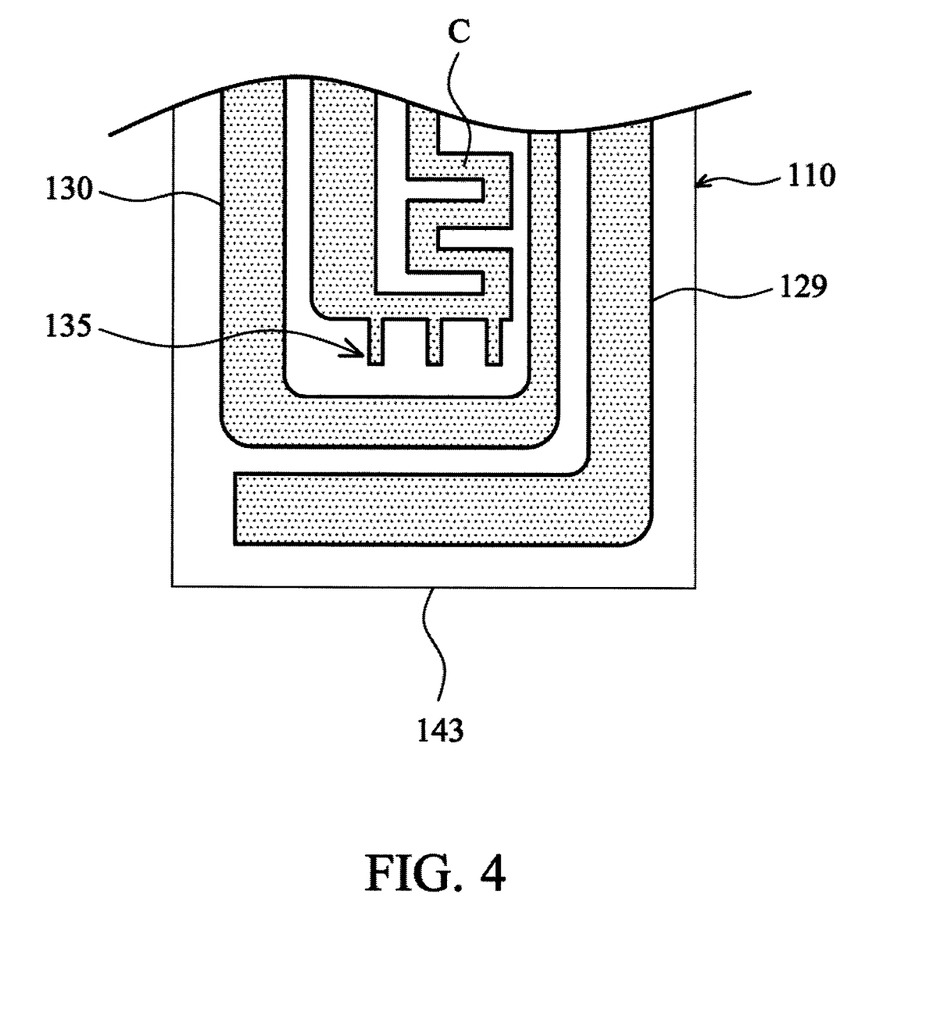
FIG. 4 is a sectional schematic view showing a substrate and an electrode structure of an electrochemical test strip according to another embodiment of the invention.

Specifically, the shape of the protruding section 135 is not only limited to FIG. 3e, but can also be integrated into the aforesaid embodiments. As shown in FIG. 4, the protruding section 135 can also be connected to the comb-shaped structure C and extended toward the test end 143. In some embodiments, the opening of the comb-shaped structure C may also face toward the test end 143.

Figure 5A:
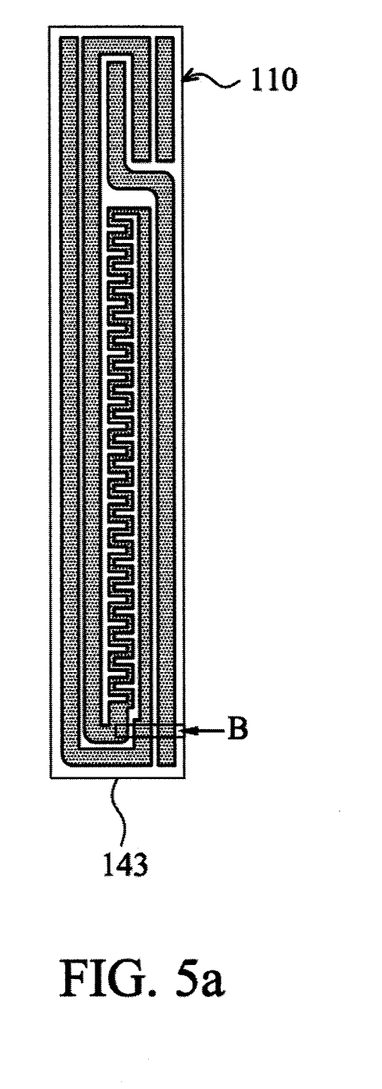
FIG. 5a is a schematic view showing a sample injection direction of an electrochemical test strip according to another embodiment of the invention.
Figure 5B:
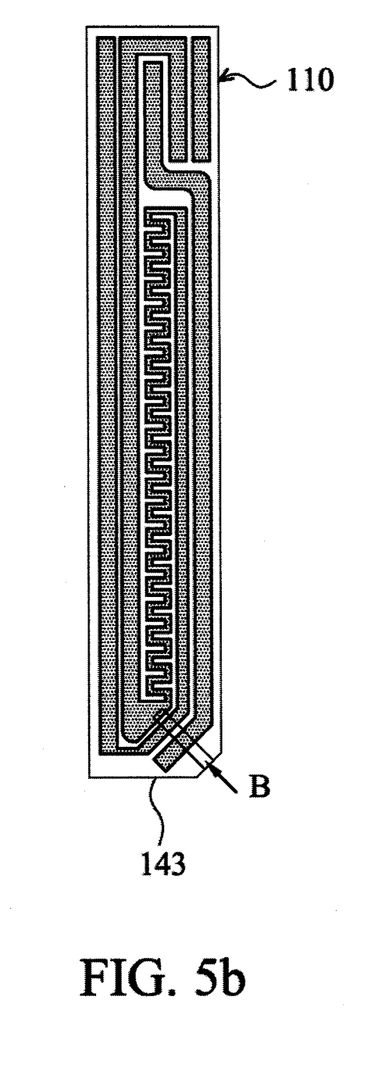
FIG. 5b is a schematic view showing a sample injection direction of an electrochemical test strip according to another embodiment of the invention.

In some embodiments, the opening 141 and the injection direction B are not perpendicular to the test end 143. As shown in FIG. 5a, the sample can be injected from a lateral side into the strip. In FIG. 5b, the sample may also be injected along an oblique direction into the strip.

In some embodiments, the electrochemical test strip may further comprises a metal layer between the electrode structure 120 and the substrate 110, wherein the metal layer may include gold, silver, palladium, platinum, nickel, copper, molybdenum, cobalt, chromium, zinc, tin, plumbum, or titanium.

In some embodiments, the working electrode 129, the first section 132, and the second section 134 of the electrochemical test strip (FIGS. 3a~3d) may respectively correspond to the first electrode 210, the second electrode 220, and third electrode 230 (the 9a, and 9b) for the underfill detection and for determining the hematocrit value and the glucose concentration of the sample.

The invention provides an electrochemical test strip comprising an auxiliary electrode with a bent portion to increase the resistance thereof. As the electrochemical test strip does not require different materials to produce electrodes (the electrode structure can be produced by the same material), the cost thereof can be effectively reduced.

While the disclosure has been described by way of example and in terms of the preferred embodiments, it is to be understood that the disclosure is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. An electrochemical test strip, comprising:
a substrate, comprising a test end;
an electrode structure, formed on the substrate, comprising:
a first electrode;
a second electrode, comprising a first end, a second end, an extension portion, and a bent portion, wherein the extension portion is connected between the first end and the bent portion, the bent portion is connected to the second end, and the extension portion and the first electrode define a space therebetween for receiving the bent portion; and
an insulative layer, covering at least a part of the electrode structure and forming an opening corresponding to the test end, wherein a sample is injected through the opening into the electrochemical test strip and sequentially contacts the first electrode and the second electrode;
wherein a testing voltage is applied between the first electrode and the second electrode for electrochemical measurement of the sample;
wherein the bent portion comprises a first section, a second section and a connecting section, wherein the first section is connected between the extension portion and the connecting section, the second section is connected between the second end and the connecting section, and the first section, the second section, and the connecting section form a U-shaped structure;
wherein the bent portion further comprises a protruding section, and the protruding section is connected to the second section and extended toward the test end.

2. The electrochemical test strip as claimed in claim 1, wherein the electrode structure comprises metal material.

3. The electrochemical test strip as claimed in claim 1, wherein the electrode structure comprises non-metal material.

4. The electrochemical test strip as claimed in claim 3, wherein the electrode structure comprises carbon.

5. The electrochemical test strip as claimed in claim 1, wherein the electrochemical test strip further comprises a metal material layer disposed between the electrode structure and the substrate.

6. The electrochemical test strip as claimed in claim 5, wherein the metal material layer comprises gold, silver, palladium, platinum, nickel, copper, molybdenum, cobalt, chromium, zinc, tin, plumbum, or titanium.

7. An electrochemical test strip, comprising:
a substrate, comprising a test end;
an electrode structure, formed on the substrate, comprising:
a first electrode;
a second electrode, comprising a first end, a second end, an extension portion, and a bent portion, wherein the extension portion is connected between the first end and the bent portion, the bent portion is connected to the second end, and the extension portion and the first electrode define a space therebetween for receiving the bent portion; and
an insulative layer, covering at least a part of the electrode structure and forming an opening corresponding to the test end, wherein a sample is injected through the opening into the electrochemical test strip and sequentially contacts the first electrode and the second electrode;
wherein a testing voltage is applied between the first electrode and the second electrode for electrochemical measurement of the sample;
wherein the bent portion comprises a first section, a second section and a connecting section, wherein the first section is connected between the extension portion and the connecting section, the second section is connected between the second end and the connecting section, and the first section, the second section, and the connecting section form a U-shaped structure;
wherein the bent portion comprises a first section, a second section and a connecting section, wherein the first section is connected between the extension portion and the connecting section, the second section is connected between the second end and the connecting section, and the connecting section forms a U-shaped structure with an opening toward a direction perpendicular to the first and second sections.

8. An electrochemical test strip, comprising:
a substrate, comprising a test end;
an electrode structure, formed on the substrate, comprising:
a first electrode;
an second electrode, comprising a first end, a second end, an extension portion, and a bent portion, wherein the extension portion is connected between the first end and the bent portion, the bent portion is connected to the second end, and the extension portion and the frist electrode define a space therebetween for receiving the bent portion; and
an insulative layer, covering at least apart of the electrode structure and forming an opening corresponding to the test end, wherein a sample is injected through the opening into the electrochemical test strip and sequentially contacts the first electrode and the second electrode;
wherein a testing voltage is applied between the first electrode and the second electrode for electrochemical measurement of the sample;
wherein the bent portion comprises a first section, a second section and a connecting section, wherein the first section is connected between the extension portion and the connecting section, the second section is connected between the second end and the connecting section, and the connecting section forms a U-shaped channel therein.

9. An electrochemical test strip, comprising:
a substrate, comprising a test end;
an electrode structure, formed on the substrate, comprising:
a first electrode;
a second electrode, comprising a first end, a second end, an extension portion, and a bent portion, wherein the extension portion is connected between the first end and the bent portion, the bent portion is connected to the second end, and the extension portion and the first electrode define a space therebetween for receiving the bent portion; and
an insulative layer, covering at least a part of the electrode structure and forming an opening corresponding to the test end, wherein a sample is injected through the opening into the electrochemical test strip and sequentially contacts the first electrode and the second electrode;
wherein a testing voltage is applied between the first electrode and the second electrode for electrochemical measurement of the sample;
wherein the bent portion comprises a first section, a second section and a connecting section, wherein the first section is connected between the extension portion and the connecting section, the second section is connected between the second end and the connecting section, and the connecting section forms a comb-shaped structure.

10. A method for testing a sample by an electrochemical test strip, wherein the electrochemical test strip includes a first electrode, a second electrode insulated from the first electrode, and a third electrode connected to the second electrode, the method comprising:
applying a first testing voltage between the second and third electrodes;
recording a background current value between the second and third electrodes according to the first voltage;
applying a second testing voltage between the first and second electrodes;
recording a first time when the sample flows through the first electrode to the second electrode;
applying a third testing voltage between the second and third electrodes and recording a current signal between the second and third electrodes according to the first voltage;
recording a second time when the current signal has a slope exceeding a predetermined value due to the sample flowing through the second electrode to the third electrode;
calculating a time period from the first time to the second time;
calculating a hematocrit value of the sample according to the time period; and
determining if the electrochemical test strip is underfilled with the sample according to a difference between the background current value and the current signal.

11. The method as claimed in claim 10, further comprising the step of:
measuring a glucose concentration of the sample and calibrating the glucose concentration by the hematocrit value if the difference between the background current value and the current signal exceeds a threshold value.

12. The method as claimed in claim 10, further comprising the step of:
prompting the user to change the electrochemical test strip if the difference between the background current value and the current signal is less than a threshold value.

* * * * *